United States Patent
Fleenor et al.

(10) Patent No.: US 6,666,859 B1
(45) Date of Patent: *Dec. 23, 2003

(54) SELF-LIMITING ELECTROSURGICAL RETURN ELECTRODE

(75) Inventors: Richard P. Fleenor, Englewood, CO (US); David B. Kieda, Salt Lake City, UT (US); James D. Isaacson, Salt Lake City, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/238,085

(22) Filed: Sep. 9, 2002

Related U.S. Application Data

(63) Continuation of application No. 09/569,998, filed on May 12, 2000, now Pat. No. 6,454,764, which is a continuation-in-part of application No. 09/201,998, filed on Nov. 30, 1998, now Pat. No. 6,083,221, which is a continuation-in-part of application No. 08/741,468, filed on Oct. 30, 1996, now abandoned.

(51) Int. Cl.⁷ .............................................. A61B 18/16
(52) U.S. Cl. ........................... 606/32; 606/35; 607/152; 128/908
(58) Field of Search .............................. 606/32, 35, 39; 607/152; 128/908

(56) References Cited

U.S. PATENT DOCUMENTS

| | | | |
|---|---|---|---|
| 3,089,496 A | 5/1963 | Degelman | 128/303.14 |
| 3,543,760 A | 12/1970 | Bolduc | 128/416 |
| 3,720,209 A | 3/1973 | Bolduc | 128/2.06 E |
| 3,848,600 A | 11/1974 | Patrick, Jr. et al. | 128/303.13 |
| 4,088,133 A | 5/1978 | Twentier | 128/303.13 |
| 4,092,985 A | 6/1978 | Kaufman | 128/303.13 |
| 4,094,320 A | 6/1978 | Newton et al. | 128/303.14 |
| 4,117,846 A | 10/1978 | Williams | 128/303.13 |
| 4,166,465 A | 9/1979 | Esty et al. | 128/303.13 |
| 4,200,104 A | 4/1980 | Harris | 128/303.14 |
| 4,207,904 A | 6/1980 | Greene | 128/798 |
| 4,226,247 A | 10/1980 | Hauser et al. | 128/641 |
| 4,231,372 A | 11/1980 | Newton | 128/303.14 |
| 4,237,886 A | 12/1980 | Sakurada et al. | 128/303.13 |
| 4,237,887 A | 12/1980 | Gonser | 128/303.14 |
| 4,267,840 A | 5/1981 | Lazar et al. | 128/303.13 |
| 4,304,235 A | 12/1981 | Kaufman | 128/303.13 |
| 4,384,582 A | 5/1983 | Watt | 128/303.13 |
| 4,387,714 A | 6/1983 | Geddes et al. | 128/303.13 |
| 4,669,468 A | 6/1987 | Cartmell et al. | 128/303.13 |
| 4,770,173 A | 9/1988 | Feucht et al. | 128/303.13 |
| 4,799,480 A | 1/1989 | Abraham et al. | 128/303.13 |
| 5,352,315 A | 10/1994 | Carrier et al. | 156/267 |
| 5,354,790 A | 10/1994 | Keusch et al. | |
| 5,520,683 A | 5/1996 | Subramaniam et al. | 606/32 |
| 5,836,942 A | 11/1998 | Netherly et al. | 606/32 |
| 6,053,910 A | 4/2000 | Fleenor | |
| 6,083,221 A | 7/2000 | Fleenor et al. | |
| 6,454,764 B1 * | 9/2002 | Fleenor et al. | 606/32 |

FOREIGN PATENT DOCUMENTS

| | | |
|---|---|---|
| GB | 1 480 736 | 7/1977 |
| GB | 2 052 269 | 1/1981 |

OTHER PUBLICATIONS

Wald, et al., "Accidental Burns Associated With Electrocautery," JAMA, Aug. 16, 1971, vol. 217, No. 7, pp. 916–921.

* cited by examiner

Primary Examiner—Lee Cohen
(74) Attorney, Agent, or Firm—Workman Nydegger

(57) ABSTRACT

A self-limiting electrosurgical return electrode for use with electrosurgery. Through selection of impedance characteristics for the materials of the principal body of the electrode, and through tailoring of electrode geometries, the electrode is self-regulating and self-limiting as to current density and temperature rise to prevent patient trauma. The return electrode includes a sheet of material having an effective bulk impedance equal to or greater than about 4,000Ω.cm and one or more connectors for making electrical connection to the sheet. The effective bulk impedance of the sheet may arise from resistive components, capacitive components, inductive components, or combinations thereof. Configuration of the return electrode allows the electrode to self-limit the electrode's current densities, thereby preventing burning of a patient during surgery. Through employment of washable surface areas, the electrode is made readily cleanable, disinfectable, sterilizable, and reusable. An optional sleeve is provided for cooperative use with the electrode.

20 Claims, 9 Drawing Sheets

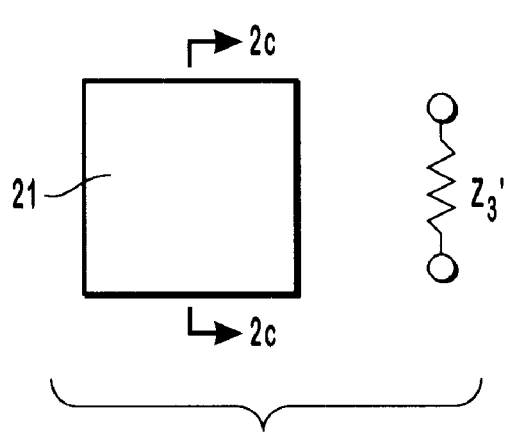
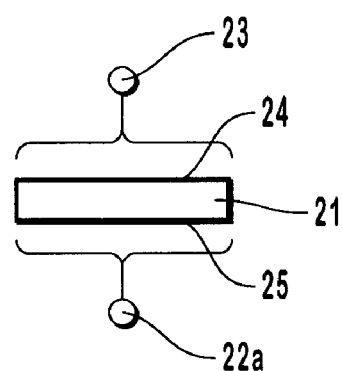
FIG. 2B  FIG. 2C
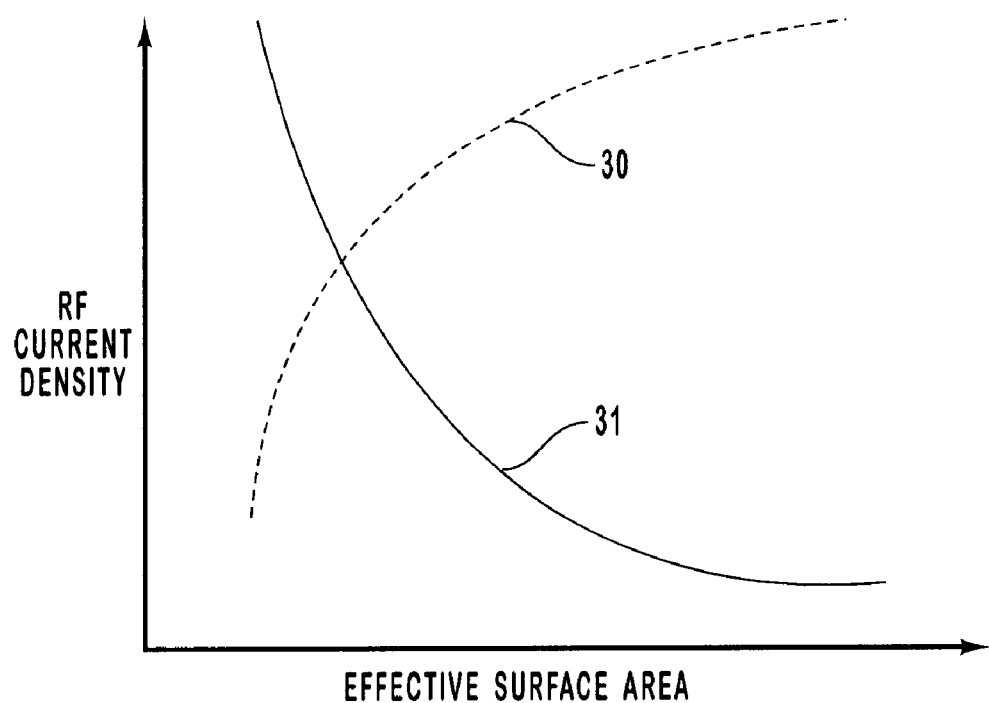
FIG. 3

SELF-LIMITING ELECTROSURGICAL RETURN ELECTRODE

RELATED APPLICATIONS

This is a continuation of U.S. patent application Ser. No. 09/569,998, filed May 12, 2000, now U.S. Pat. No. 6,454,764, and entitled "Self-limiting Electrosurgical Return Electrode," that is a continuation-in-part of Ser. No. 09/201,998 U.S. Pat. No. 6,083,221, filed Nov. 30, 1998, and entitled "Resistive Reusable Electrosurgical Return Electrode," that is a continuation-in-part application of U.S. patent application Ser. No. 08/741,468, filed Oct. 30, 1996, now abandoned, and entitled "Reusable Electrosurgical Return Pad." Reference is made to U.S. patent application Ser. No. 09/769,025, filed Jan. 24, 2001, now U.S. Pat. No. 6,582,421 and entitled "Capacitive Reusable Electrosurgical Return Electrode", that is a continuation-in-part application of U.S. Pat. No. 6,214,000, filed Nov. 6, 1999, and entitled "Capacitive Reusable Electrosurgical Return Electrode", and U.S. Pat. No. 6,053,910, filed Oct. 30, 1996, and entitled "Capacitive Reusable Electrosurgical Return Electrode," the disclosures of which are incorporated by this reference.

BACKGROUND OF THE INVENTION

1. The Field of the Invention

This invention relates to electrosurgery and, more particularly, to return electrodes that are adapted for providing effective and safe electrosurgical energy return without conducting or dielectric gels, which may be reusable and/or disposable.

2. The Relevant Technology

As is known to those skilled in the art, modern surgical techniques typically employ radio frequency (RF) power to cut tissue and coagulate bleeding encountered in performing surgical procedures. For historical perspective and details of such techniques, reference is made to U.S. Pat. No. 4,936,842, issued to D'Amelio et al., and entitled "Electroprobe Apparatus," the disclosure of which is incorporated by this reference.

As is known to those skilled in the medical arts, electrosurgery is widely used and offers many advantages including the use of a single surgical tool for both cutting and coagulation. Every monopolar electrosurgical generator system must have an active electrode which is applied by the surgeon to the patient at the surgical site to perform surgery and a return path from the patient back to the generator. The active electrode at the point of contact with the patient must be small in size to produce a high current density in order to produce a surgical effect of cutting or coagulating tissue. The return electrode, which carries the same current as the active electrode, must be large enough in effective surface area at the point of communication with the patient such that a low density current flows from the patient to the return electrode. If a relatively high current density is produced at the return electrode, the temperature of the patient's skin and tissue will rise in this area and can result in an undesirable patient burn.

In 1985, the Emergency Care Research Institute, a well-known medical testing agency, published the results of testing it had conducted on electrosurgical return electrode site burns, stating that the heating of body tissue to the threshold of necrosis occurs when the current density exceeds 100 milliamperes per square centimeter.

The Association for the Advancement of Medical Instrumentation ("AAMI") has published standards that require that the maximum patient surface tissue temperature adjacent an electrosurgical return electrode shall not rise more than six degrees (6°) Celsius under stated test conditions.

Over the past twenty years, industry has developed products in response to the medical need for a safer return electrode in two major ways. First, they went from a small, about 12×7 inches, flat stainless steel plate coated with a conductive gel placed under the patient's buttocks, thigh, shoulders, or any location where gravity can ensure adequate contact area to a flexible electrode. These flexible electrodes, which are generally about the same size as the stainless steel plates, are coated with a conductive or dielectric polymer and have an adhesive border on them so they will remain attached to the patient without the aid of gravity, and are disposed of after use. By the early 1980's, most hospitals in the United States had switched over to using this type of return electrode. These return electrodes are an improvement over the old steel plates and resulted in fewer patient return electrode burns but have resulted in additional surgical costs in the United States of several tens of millions of dollars each year. Even with this improvement, hospitals were still experiencing some patient burns caused by electrodes that would accidentally fall off or partially separate from the patient during surgery.

Subsequently, there was proposed a further improvement, an Electrode Contact Quality Monitoring System that would monitor the contact area of the electrode that is in contact with the patient and turn off the electrosurgical generator whenever there was insufficient contact area. Such circuits are shown, for example, in U.S. Pat. No. 4,231,372, issued to Newton, and entitled "Safety Monitoring Circuit for Electrosurgical Unit," the disclosure of which is incorporated by this reference. This system has resulted in additional reduction in patient return electrode burns, but requires a special disposable electrode and an added circuit in the generator that drives the cost per procedure even higher. Fifteen years after this system was first introduced, fewer than 40 percent of all the surgical operations performed in the United States use this system because of its high costs.

SUMMARY AND OBJECTS OF THE INVENTION

The present invention overcomes the problems of the prior art by providing a return electrode that eliminates patient burns without the need for expensive disposable electrodes and monitoring circuits in specialized RF generators.

Briefly, the improved return electrode according to the preferred embodiment of the invention hereof includes an effective surface area that is larger than other return electrodes that have been disclosed or used in surgery previously. It is so large and so adapted for positioning relative to the body of a patient that it eliminates the need for conductive or dielectric gels. Moreover, the exposed surface is of a material that is readily washable and/or sterilizable so as to facilitate easy and rapid conditioning for repeated reuse. It employs geometries and materials whose impedance characteristics, at typically used electrosurgical frequencies, are such that it self-limits current densities (and corresponding temperature rises) to safe thresholds, should the effective area of the working surface of the electrode be reduced below otherwise desirable levels. Accordingly, the need for the foregoing expensive monitoring circuits in specialized RF generators is eliminated.

In accordance with a feature of the invention, an electrosurgical return electrode is made sufficiently large to present sufficiently low electrical impedance and low current densities at typical electrosurgery frequencies used in medical procedures to reduce the possibility of excessive temperature elevation in adjacent patient tissue, (i.e., by maintaining temperature ("T") rise below six degrees (6°) Celsius) thereby avoiding tissue necrosis or other undesired patient trauma.

In accordance with yet another feature of the invention, the working surface of the electrode (the electrode surface that is in contact with or in close proximity to the patient) is made sufficiently large in area so that in normal use, current flow will not be reduced to a point where it impedes the surgeon's ability to perform surgery at the surgical site.

In accordance with yet another feature of the invention, in one embodiment, the electrosurgical return electrode is a simple single-layer construction, thus minimizing cost.

In accordance with yet another feature of the invention, in one embodiment, controlled electrical conductivity is imparted to the single layer of material by the inclusion therein of electrically conductive materials such as conductive threads or carbon black, thus conditioning conductivity as a function of surface area to levels which limit passage of current therethrough to safe values.

In accordance with yet another feature of the invention, in another embodiment, a moisture impervious working surface is provided for positioning adjacent an adjoining surface of the body of a patient, thus facilitating cleansing and reuse of the electrosurgical electrode.

In accordance with yet another feature of the invention, the aforementioned moisture impervious working surface is made resistant to normally encountered cleaning, disinfecting, and sterilizing agents, thus further facilitating cleansing and reuse.

In accordance with yet another feature of the invention, in another embodiment, a sleeve is provided for cooperative use with the electrosurgical electrode, thus protecting the electrode from inadvertent damage that might occur, for example, from accidental contact of the active electrosurgical instrument with the electrode surface.

In accordance with yet another feature of the invention, the electrical impedance of the materials in and adjacent to the working surface of the electrode is sufficiently elevated so as to limit current density at the working surface to a level below the threshold of patient tissue trauma, thus providing a self-limiting characteristic to prevent patient trauma in the event of accidental reduction of the effective working surface of the electrode.

In accordance with yet another feature of the invention, in one embodiment, the electrosurgical electrode is form-fitted to the operating table on which the electrosurgical procedure is to be performed, thus facilitating realization of other features of the invention.

These and other objects and features of the present invention will become more fully apparent from the following description and appended claims, or may be learned by the practice of the invention as set forth hereinafter.

BRIEF DESCRIPTION OF THE DRAWINGS

FIG. 2B is an enlargement of a segment of the electrosurgical return electrode of FIG. 2A;

FIG. 2C is a cross section taken along the section lines 2C—2C of FIG. 2B and illustrating the effective circuit impedance represented by the segment of 2B;

FIG. 3 is a chart illustrating in graphical form the relationships between effective surface area of the return electrode and the effective radio frequency current density developed at the electrode;

DETAILED DESCRIPTION OF THE PREFERRED EMBODIMENTS

Figure 1:
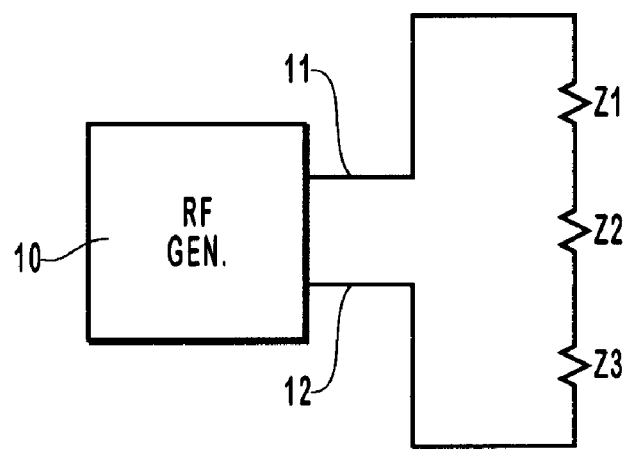
FIG. 1 is a simplified electrical schematic diagram illustrating typical impedances effectively included in the operative path of radio frequency current flow as presented to an electrosurgical generator during an operative procedure.

Now turning to the drawings, and more particularly FIG. 1 thereof, it will be seen to depict a simplified electrical schematic diagram illustrating typical impedances effectively included in the operative path of radio frequency current flow as presented to an electrosurgical generator during an operative procedure. There, it will be seen are conventional radio frequency electrical power generator 10, such as but not limited to constant power, voltage, and/or current or variable power, voltage and/or current. Connected to electrical power generator 10 are conventional electrical conductors 11 and 12 which respectively connect the generator 10 to the surgeon's implement represented by impedance $z_1$ and an electrosurgical return electrode represented by impedance $z_3$. Impedance $z_2$ is provided to represent the impedance presented by the patient's tissue lying between the operation site and the return electrode. Electrical conductors 11 and 12 are representative of one illustrative structure that is capable of performing the function of connecting means for making electrical connection to the sheet. It may be appreciated by one skilled in the art, however, that various other structures are appropriate and capable of performing the desired function.

Although the diagram of FIG. 1 is simplified and generally considers circuit elements in terms of the principal resistances, including the reactances contributed by the surgical instrument, the patient's body and the return electrode, so as to clearly and succinctly illustrate principles of the invention, it should be understood that in reality certain other parameters would be encountered, parameters such as distributed inductance and distributed capacitance which, for purposes of clarity in illustration of the principles hereof, are deemed relatively small and so not considered at this point in this description. However, as set forth below, in one embodiment when an insulating sleeve is interposed between the electrode and the body of a patient, a significant element of capacitive reactance may be included in the impedance of $Z_3$. It should also be noted that FIGS. 1–10 are intentionally simplified so as to present the principles of the invention succinctly, with a more rigorous and complete discussion being presented in connection with FIGS. 11–17.

The initial embodiment, hereof, is that of an electrode operating in a combined resistive and/or capacitive mode. Accordingly, if the relatively small stray capacitive and inductive reactances are disregarded, the total effective impedance of the circuit will be equal to the sum of the individual impedances $z_1$, $z_2$ and $z_3$; and since essentially the same current will pass through all three, the voltage generated by RF generator 10 will be distributed across impedances $z_1$, $z_2$ and $z_3$ in direct proportion to their respective values. Thus, the energy released in each of such components will also be directly proportional to their values.

Since it is desired that developed energy be concentrated in the region where the surgeon's implement contacts the patient's tissue, it is desirable that the resistive component of the impedance represented by $z_1$ be substantial and that current passing therethrough (and consequent energy release) be concentrated in a very small region. The latter is accomplished by making the region of contact with the patient at the operative site very small.

It is known that, in contrast with the foregoing series circuit, components of combined resistive and capacitive reactance, when connected in parallel, present a total effective impedance that is given by the formula:

$$Z_{eff} = \frac{1}{\frac{1}{z_1}+\frac{1}{z_2}+\frac{1}{z_3}+\frac{1}{z_4}+\frac{1}{z_5}+\frac{1}{z_6}} \quad (1)$$

Thus, if 100 similar impedances, each of 100 ohms, were connected in parallel, the effective impedance $Z_{eff}$ would equal one ohm. If half of such impedances were effectively disconnected, the remaining effective impedance would be two ohms, and if only one of the impedances were active in the circuit, the remaining effective impedance would be 100 ohms. The significance of these considerations and their employment to render the electrode hereof self-limiting and fail-safe will be evident from the following description of the elements illustrated in FIGS. 2A, 2B, 2C and 3.

Figure 2A:
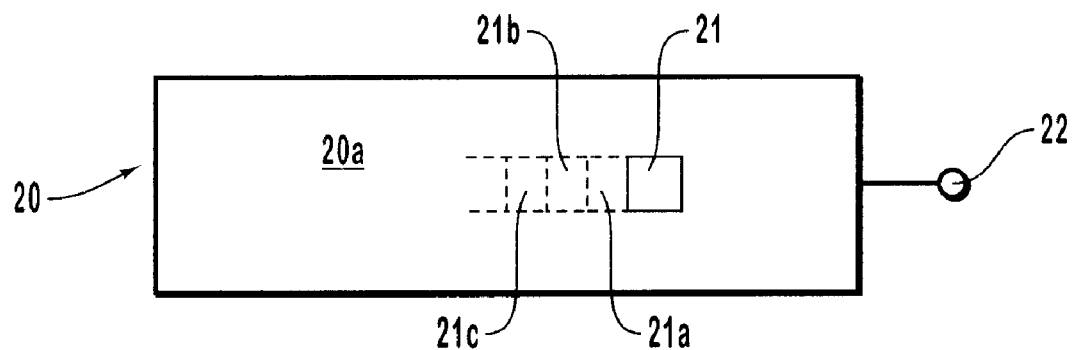
FIG. 2A is a top view of a wide-area distributed electrosurgical return electrode illustrating the principles of the invention.

Now turning to FIG. 2A, there will be seen a schematic representation of the top view of a wide-area distributed electrosurgical return electrode 20 illustrating the principles of the invention. At the right hand side of the figure there is shown an electrical connection terminal 22 to facilitate connection to an electrical return conductor, such as conductor 12 of FIG. 1.

The surface 20a of return electrode 20 is preferably smooth and homogeneous and includes a thin resistive and/or dielectric layer 21a (FIG. 2C). Alternatively, surface 20a of return electrode 20 may include a capacitive and/or inductive layer, depending on the particular operation of return electrode 20. For instructional purposes of this description and to aid in the mathematical modeling of return electrode 20, electrode 20 may be thought of as including a plurality of uniformly-sized regions or segments as represented by regions 21, 21a, 21b, 21c . . . 21n. It will be appreciated by one skilled in the art, however, that return electrode may or may not include discontinuous regions or segment, it being preferred that electrode 20 have continuous segments.

Region/segment 21 is shown larger in FIG. 2B in order to be similar in scale to the resistive impedance $z_3'$ it represents. It thus will now be evident that each of the segments of electrode 20 corresponding to segments 21 . . . 21n inherently has the capability of presenting an impedance similar to that of impedance $z_3'$. However, the number of such segments which are effectively active in parallel within the circuit is a direct function of the surface area of the patient that overlies the electrode. Thus, in the case of a large supine patient whose body is in effective contact with 50 percent (50%) of the upper surface of the electrode, 50 percent of the segments corresponding to segments 21–21n will be effectively paralleled in the circuit to form an impedance represented by impedance $z_3$ of FIG. 1; and, accordingly, if electrode 20 contains 100 segments of 100 ohms each, the effective impedance operatively presented by the effective 50 percent of the electrode elements would be 2 ohms. Since 2 ohms is very small compared with the impedance represented by elements $z_1$ and $z_{2'}$, very little energy is dissipated at the region of contact between the patient and the electrode, and due also to the relatively large effective working area of the electrode, current density, and temperature elevation are maintained below the danger thresholds mentioned above.

Now, if for any reason, the effective contact area between the patient and electrode were to be reduced to the surface of only one of the segments 21–21n, then the effective impedance (combined capacitive reactance and resistance in the example under consideration) would increase to 100 ohms; and at some point of reduction in contact area, the effective impedance would rise to a level relative to the impedance presented at the site of the electrosurgical instrument so as to diminish the electrosurgical effect of the surgical instrument or otherwise prevent effective use of the instrument by the surgeon, thus signaling the surgeon that the patient should be repositioned so as to present a greater surface area in contact with the return electrode. At the same time, the total circuit impedance would be increased so that the total current that would flow if the surgeon attempted to employ his instrument without repositioning the patient would be reduced to a value below that which would cause undesired trauma to the patient. Accordingly, there is provided a self-limiting feature that enhances safety in use without the need for the aforementioned separate circuit monitoring and control circuits.

FIG. 2C is a cross section taken along the section lines 2C—2C of FIG. 2B and illustrates the effective circuit impedance $z_3'$ represented by the segment 21 of 2B. In FIG.

2C there are seen small segment 21 with its upper patient-contacting surface 24 represented electrically by terminal 23 and its lower surface 25 represented by electrical terminal 22a. For the purpose of this description (and in order to present the principles underlying this embodiment clearly), the impedance $z_3'$ may be thought of as existing between terminals 23 and 22a. Of course, it will be evident to those skilled in the art that in an embodiment in which a thin but highly conductive layer is included along the lower surface of electrode 20, each of the impedances represented by the remaining segments are connected at their lower extremities in parallel to terminal 22; whereas, if such highly conductive layer is absent, then, in addition to the impedance represented by the material lying between the upper and lower regions of each segment, there will be an additional impedance (not shown) that is represented by the material through which current would have to pass transversely or laterally through the electrode in order to get to terminal 22.

It should now be evident that if lateral impedance is minimized by provision of the aforementioned thin conducting layer, or if the effective conductivity at the lower part of the material of region 21 is otherwise increased, the effective impedance presented by the return electrode will be inversely proportional to the effective upper surface of the electrode that is in contact with a patient.

FIG. 3 is a chart generally illustrating in graphic form the relationships between the effective surface area of the return electrode and the effective radio frequency current densities developed at the electrode. However, before proceeding to a consideration of such chart, it should be noted that the chart is simplified so as to illustrate the principles underlying the invention and does not represent actual data that may vary substantially. In FIG. 3 there is seen a plot of RF Current Density versus Electrode Effective Surface Area, the latter (as should now be evident to those skilled in the art) being that part of the surface of the return electrode that makes effective electrical contact with the body of a patient. As would be expected from the foregoing discussion, when the effective area is large, the current at the surgeon's implement is high (dashed graph line 30) and the corresponding current density across the return electrode is very low (solid graph line 31). This is, of course, the condition desired for conducting surgery. However, if we assume constant current throughout the circuit, as the effective surface area decreases, the current density across the return electrode (solid graph line 31) increases with a corresponding decrease in the current at the surgeon's instrument (dashed graph line 30). When the effective surface area declines to some predetermined point, there will remain insufficient current at the surgical instrument to effectively conduct surgery.

It may be appreciated by one skilled in the art that the change in current density and available current to the surgeon may or may not occur simultaneously with the variations in effective surface area. Various embodiments of the present invention may have substantially simultaneous changes in current density and available current, while other embodiments of the present invention may include a lag period therebetween.

The parameters selected for the materials and electrode dimensions are chosen so that current density and corresponding tissue temperature elevation adjacent the return electrode do not exceed the limits mentioned in the introduction hereof. It will now be seen that by a proper selection of such parameters the return electrode is made self-limiting, thereby obviating the need for the additional monitoring circuits to which reference is made above.

To facilitate description of the principles underlying the invention, the foregoing is described in terms of impedances whose principal components are resistances and capacitive reactances. However, the principles of the invention are also applicable to other embodiments in which the impedances include any combination of resistive, capacitive and/or inductive impedances.

The invention hereof is now further described in connection with applications in which an effective dielectric layer is represented by a physical dielectric layer on the upper surface of the electrode, by the material of a surgical gown worn by the patient, by a bed sheet or other operating room linens interposed between the patient and the return electrode, by the material of a protective sleeve fitted over the return electrode, or any combination thereof.

Figure 4:
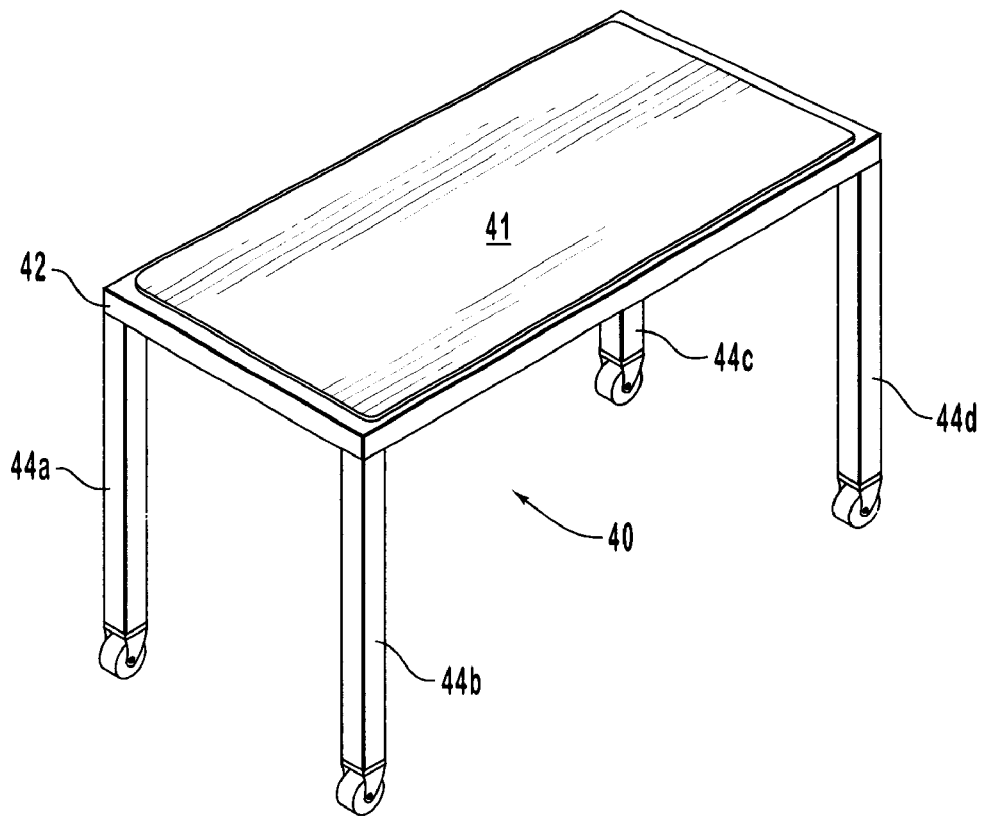
FIG. 4 is a perspective view showing an operating table with the electrosurgical return electrode according to the invention disposed on the upper surface thereof.

Reference is now made to FIG. 4, which illustrates in perspective an operating table 40 with an electrosurgical return electrode 41 according to the invention disposed on the upper surface thereof, an edge of which is identified by the numerals 42. The operating table is shown to have conventional legs 44a–44d that may be fitted with wheels or rollers as shown. Table 40 is one structure that is capable of performing the function of supporting means for supporting a patient during treatment. It may be appreciated by one skilled in the art, however, that various other configurations of support means are possible and capable of performing the required function. For example, supporting means may include but not be limited to chairs, plates, beds, carts, and the like.

Figure 5:
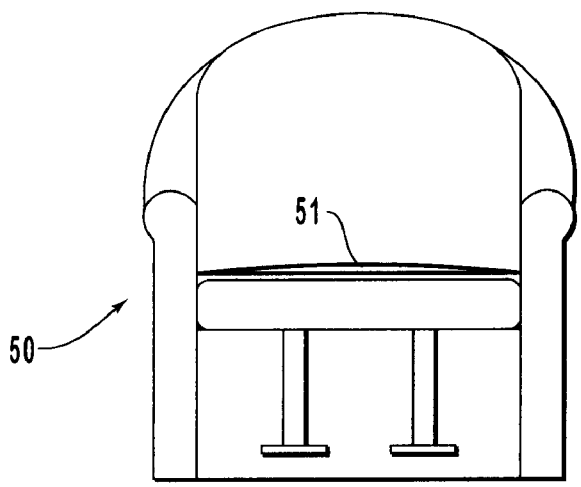
FIG. 5 is a front view illustrating a surgical chair with an electrosurgical return electrode according to the invention disposed on the surface of the seat thereof.

Although in FIG. 4, the entire upper surface of the table is shown as being covered with return electrode 41, it should be understood that entire coverage is by no means required in order to practice the principles of the invention. Thus, when used with conventional electrosurgical generators, the return electrode needs only to present an effective working surface area which is sufficient to provide adequate resistive, capacitive, or inductive coupling at the typically employed RF frequencies so as not to interfere with the surgeon's ability to perform surgery while at the same time avoiding undesired tissue damage. It has been found that at conventional electrosurgical frequencies, this has necessitated only an effective working surface area no larger than about the projected outline of one-half of the torso for an adult patient lying on an operating table or the buttocks of a patient sitting in a chair such as is illustrated in FIG. 5. However, the effective working surface area will vary depending on the material used, in some geometrical configurations, and in instances where various layers of operating room linens are placed over the electrode. The principles hereof may be successfully employed and the effective working surface area of the return electrode determined in such circumstances by routine experimentation. Under certain conditions, the effective working surface may be as small as about seven square inches (or about 45 square centimeters).

Moreover, although the return electrodes shown in FIGS. 6–8, and 10 are depicted as being rectangular in shape, it will be evident that they could be oval or contoured as, for example, to follow the silhouette of the torso or other principal part of the body of a patient. As will be evident from the foregoing, it is important that the electrode be configured so that when the electrode is used: (1) the return current density on the surface of the patient is sufficiently low; (2) the electrical impedance between the electrode and the patient is sufficiently low so that electrical energy is not concentrated sufficiently to heat the skin of the patient at any location in the electrical return path by more than six degrees (6°) Celsius; and (3) the characteristics of the materials and geometries are such that if the effective area of the electrode is reduced below a selected threshold level, there will be insufficient energy dissipated at the surgeon's implement for him to continue effectively using the implement in its electrosurgical mode.

As will be recognized by those skilled in the art, it is not necessary for there to be direct ohmic contact between the skin of a patient and the return electrode hereof for the electrode to perform generally according the foregoing description, for although capacitive reactance (represented by the distance between a patient's body and the electrode) will be introduced if something such as a surgical gown separates them, such capacitive reactance will modify rather than destroy the impedance identified as $z_3$.

As is known to those skilled in the art, in an alternating current circuit (e.g., such as those used in electrosurgery) the capacitive reactance of an impedance is a function both of capacitance and the frequency of the alternating current electrical signal presented to the reactance. Thus, the formula for capacitive reactance (in ohms) is $$X_c = \frac{1}{2\pi fC} \qquad (2)$$

where Xc is capacitive reactance in ohms, π is 3.14159, f is frequency in hertz, and C is capacitance in farads.

The formula for capacitance in a parallel plate capacitor is:

$$C = \frac{\kappa \varepsilon_0 A}{t} \qquad (3)$$

where C is capacitance in Farads, κ is the dielectric constant of the material lying between the effective plates of the capacitor, A is the area of the smallest one of the effective plates of the capacitor in square meters, t is separation of the surfaces of the effective plates in meters, and $\varepsilon_0$ is the permittivity of air in Farads/meter. Thus, it will be seen that to meet maximum permissible temperature rise criteria in an embodiment in which electrode circuit capacitance is substantial, different minimum sizes of electrodes may be required depending upon the frequency of the electrical generator source, the separation of the body of the patient from the electrode, and the material lying between the effective conductive region of the electrode and the adjacent body surface. Accordingly, although the principles of the invention are applicable to a wide range of frequencies of electrosurgical energy, the considerations set forth herein for minimum sizes of return electrodes specifically contemplate frequencies typically employed in conventional electrosurgical energy generators.

Those skilled in the art know that, with the currently used disposable return electrodes, reducing the effective size of the electrode to about three square inches will not reduce the RF current flow to a level where it will impede the surgeon's ability to perform surgery nor concentrate current to a level to cause patient trauma. However, to provide for some spacing of the electrode from patient's body, a return electrode according to the invention hereof, would need a minimum effective area of between about 7 and about 11 square inches (about 45 cm$^2$ to about 70 cm$^2$) with a relatively small separation from the skin of the patient such as that provided by a surgical gown or no interposing gown at all. Such an effective area is easy to obtain if the patient is positioned on an electrode that is the size of their upper torso or larger.

The characteristics of the desired dielectric for the present embodiment are sufficiently comparable to those of selected rubbers, plastics and other related materials that the latter may be satisfactorily employed as materials for the return electrode. As mentioned above, with such a return electrode, if the patient is positioned such that not enough of the return electrode is in close proximity to the patient to result in as low impedance as needed, the results would be that the current flow from the electrosurgical generator would be reduced to a level making it difficult for the surgeon to perform surgery. Thus, in the present embodiment, notwithstanding interposition of some additional capacitance represented by a surgical gown, the features described above will continue to occur.

As mentioned above, FIG. 5 is a front view illustrating a surgical chair 50 with an electrosurgical return electrode 51 according to the invention disposed on the upper surface of the seat thereof. Accordingly, when a patient is sitting in the chair, the buttocks and upper part of the thighs overlie and are in sufficiently close proximity to the return electrode so that coupling there between presents an impedance meeting the foregoing criteria; namely, that the electrical impedance between it and the patient is sufficiently low to allow the surgeon to perform the procedure while providing that current density is sufficiently low and that insufficient electrical energy is developed across the return impedance to heat the skin of the patient at any location in the electrical return path by more than six degrees (6°) Celsius.

Figure 6:
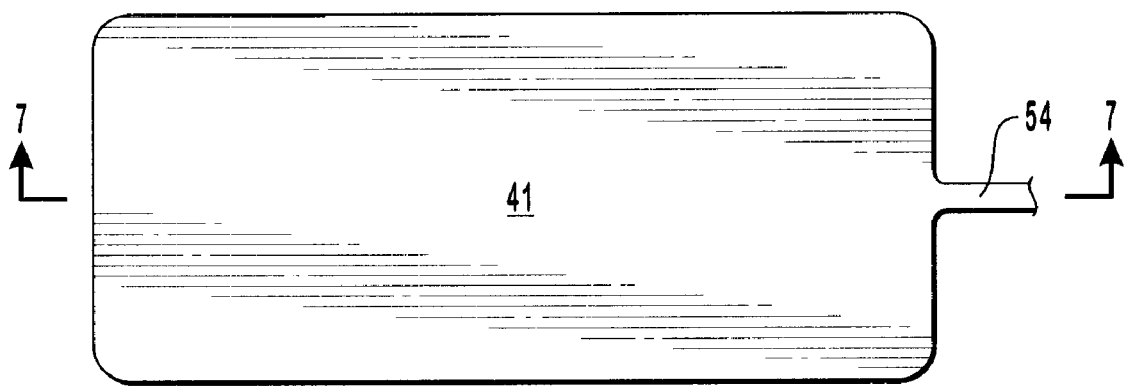
FIG. 6 is a top view of an electrosurgical return electrode according to the invention.

FIG. 6 is a top view of another electrosurgical return electrode according to the invention. It will be observed that the upper exposed, or working, surface of the electrode again is expansive so as to meet the foregoing criteria for low impedance. Although it is not necessary that the electrode cover the entire surface of an operating table or the entire seat surface of a dental or other patient chair, it has been found advantageous in some instances to provide a greater surface area than that of the projected area of the buttocks or torso of a patient so that if a patient moves position during the course of a procedure, a sufficient portion of the patient will remain in registration with the electrode surface so that the effective impedance will remain less than the above-described level.

At this juncture, it may be helpful to emphasize characteristics of the improved electrode according to the invention hereof that are deemed particularly relevant to an understanding of the inventive character thereof. First, as mentioned above, the electrode does not need to be in direct contact with a patient, either directly or through intervening conductive or nonconductive gel. In addition, because of its expansive size, there is no need for tailoring the electrode to fit physical contours of a patient. In this connection, it has been found that although with selected materials and geometries, the self-correcting and self-limiting principles hereof could be achieved in an electrode as small as about seven square inches (or about 45 square centimeters) in working surface area, the preferable range of exposed upper working surface area of the electrode lies in the range of from about 11 to 1,500 square inches (or about 70 to 9,680 square centimeters). By making the electrode several times larger (typically, at least an order of magnitude larger) in working surface area than previous proposals, the need for direct physical attachment, either directly to the skin of the patient or through gels, is eliminated.

The electrode according to the invention hereof, as illustrated in FIG. 6, may be made of conductive plastic, rubber, or other flexible material which, when employed in the electrode will result in an effective dc resistance presented by each square centimeter of working surface to be greater than about 8000Ω. Silicone or butyl rubber have been found to be particularly attractive materials as they are flexible, as well as readily washable and sterilizable. Alternatively, the main body of the return electrode may be made of inherently relatively high resistance flexible material altered to provide the requisite conductivity. A preferred example of the latter is that of silicone rubber material in which there are impregnated conductive fibers, such as carbon fiber, or in which there have been distributed quantities of other conductive substances such as carbon black, quantities of gold, silver, nickel, copper, steel, iron, stainless steel, brass, aluminum, or other conductors.

Further reference to FIG. 6 reveals the presence of a conventional electrical connector 54 attached to the electrode 41 to provide a conventional electrical return to the electrosurgical radio frequency energy source (not shown). Connector 54 is another structure capable of performing the function of connecting means for making electrical connection to the sheet. Connector 54 is only illustrative of one possible structure for performing the desired function; it being appreciated by one skilled in the art that various other structures are capable of performing the required function.

Figure 7:
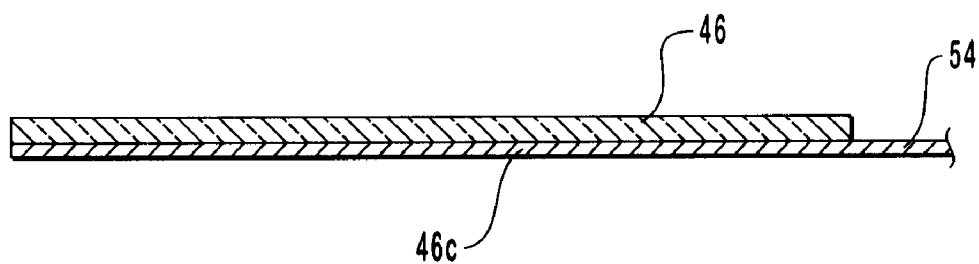
FIG. 7 is a section taken along the lines 7—7 of FIG. 6.

As mentioned above, FIG. 7 is a section taken along the lines 7—7 of FIG. 6. FIG. 7 shows an electrode 46 similar to electrode 20 of FIGS. 2A–2C, except that electrode 46 includes a thin highly-conductive lower stratum 46c to facilitate conduction of current outwardly to terminal 54. In one preferred form, the thickness of the electrode lies in a range from about 1/32 inch to 1/4 inch (about 0.08 cm to 0.64 cm), which, with the aforementioned range of impedance of the main body of material and the capacitive reactance of the upper dielectric layer, provides the required impedance together with desired physical flexibility for ease of use and handling.

Figure 8:
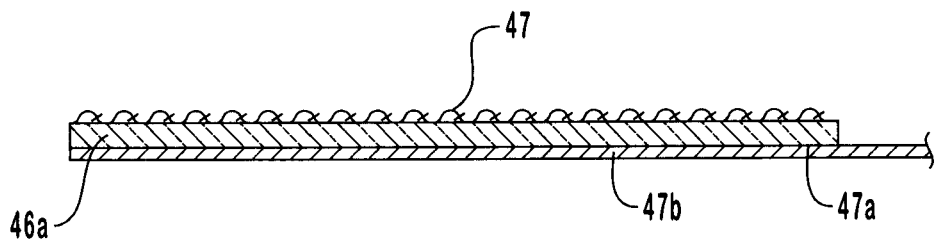
FIG. 8 is a section similar to that of FIG. 7 but illustrating the capacitance presented by a patient's surgical gown.

FIG. 8 is a section similar to that of FIG. 7, but presenting a multiple layer embodiment illustrating the separation presented by a patient's gown according to the invention hereof. There, in FIG. 8 are shown a layer 46a (similar to layer 46 of FIG. 7) and an overlying effectively capacitive layer 47 representing an insulating dielectric layer, a patient's surgical gown, an operating room linen, a protective sleeve or sheath, or any combination thereof. It should be understood that in addition to a construction similar to that of the electrode of FIGS. 6–7, a conductive layer 47a of FIG. 8 could comprise a sheet or screen of gold, brass, aluminum, copper, silver, nickel, steel, stainless steel, conductive carbon, conductive fluids, gels, saline, and the like. Further reference to FIG. 8 reveals another dielectric layer 47b covering the lower surfaces of layer 46a.

Figure 9:
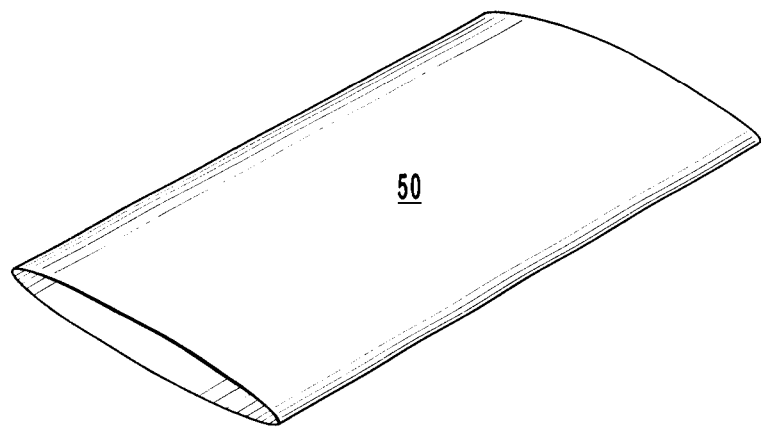
FIG. 9 is a perspective view of a cover adapted for encasing any of the embodiments of FIGS. 6–8.

FIG. 9 is a perspective view of a sleeve 50 adapted for encasing any one of the embodiments of FIGS. 6–8. Thus, provision is optionally made for encasing the foregoing return electrode-shaped electrodes within protective envelopes in situations in which it is desired to eliminate the need for cleaning the electrode itself by protecting it from contamination through the use of a sleeve of impervious material from which the electrode, after use, can merely be withdrawn and the sleeve discarded. As will be evident to those skilled in the art, such a sleeve may preferably be made of any of a variety of known materials, such as vinyl plastics, polyester or polyethylene.

Figure 10:
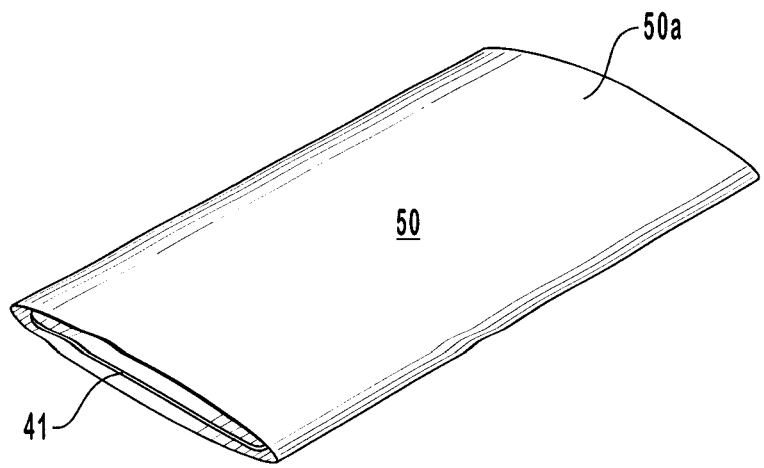
FIG. 10 is a view illustrating one of the embodiments of FIGS. 6–8 encased within the cover of FIG. 9.

FIG. 10 is a view illustrating one of the embodiments of FIGS. 6–8 encased within the sleeve of FIG. 9. There, it will be seen, is outer surface 50a of sleeve 50; and shown encased within sleeve 50 for illustrative purposes is electrode 41 of FIG. 6.

Total Electrode Ground Pad Impedance and Self-Limiting Feature

Figure 11:
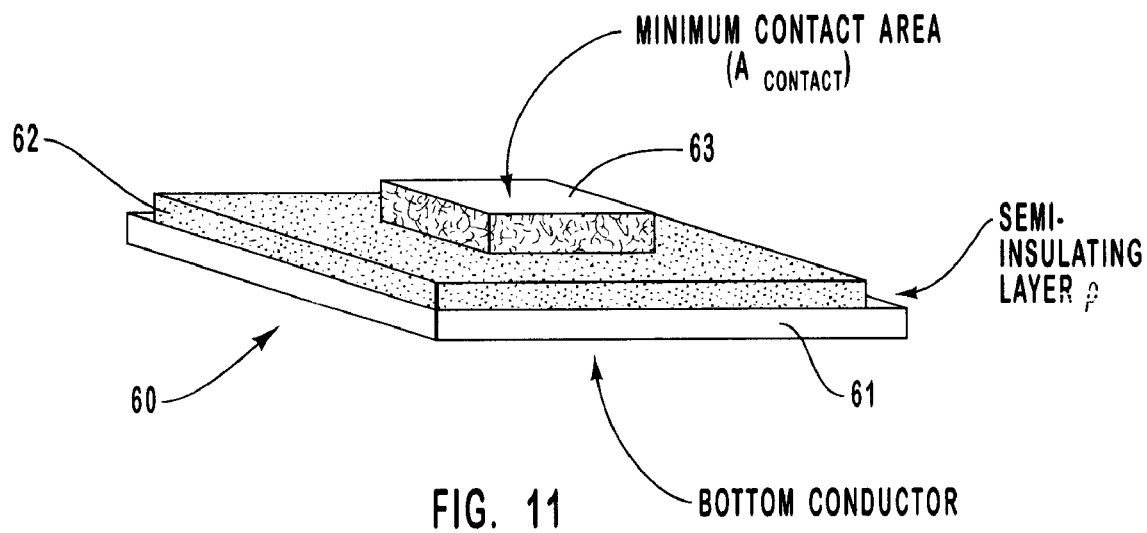
FIG. 11 is a perspective view of an electrode according to the invention illustrating a simulated condition when the effective contact area with a patient is substantially less than the physical electrode size.

FIG. 11 depicts an electrosurgical electrode 60 consisting of a conductive metal backing 61 and a semi-insulating layer 62. The electrode 60, and more specifically, semi-insulating layer 62, is in contact with another conducting layer 63 which represents a patient thereupon. The self-limiting feature of electrosurgical return electrode 60 (maintains current densities below a threshold level) arises due to the total impedance of electrode 60, whether such impedance arises from semi-insulating layer 62 alone or in combination with conductive metal backing 61 and/or conducting layer 63. Furthermore, the total impedance may arise from the various resistive, inductive, and/or capacitive components of conductive metal backing 61, semi-insulating layer 62 and/or conducting layer 63.

Electrode 60 includes a single layer of semi-insulative material 62 having a bulk resistivity ρ and thickness t. An area A placed between a conductive surface and the patient may be modeled as a resistor (R) in parallel with a capacitor (C).

For ease of explanation, we will determine the resistive requirements of electrode 60 for self-limiting in a purely resistive scenario where electrode 60 is modeled as a resistor in parallel with a capacitor. Following the calculation of the minimum requirements for self-limiting in the purely resistive case, we will generalize the analysis for any impedances, whether such impedances result from resistive, capacitive, and/or inductive components.

As such, the resultant total impedance equivalent for the resistor in parallel with the capacitor combination is $$Z_{tot} = R \| X_C = \frac{(R)\left(\frac{1}{j\omega C}\right)}{(R) + \left(\frac{1}{j\omega C}\right)} = \frac{R}{1 + j\omega CR} \tag{4}$$

where j is an imaginary component of reactance, and ω is the angular frequency and is defined as ω=2πf where f is the electrosurgical generator frequency. The magnitude of the impedance is $$|Z_{tot}| = \sqrt{\frac{R^2}{1 + \omega^2 C^2 R^2}} = R\sqrt{\frac{1}{1 + \omega^2 C^2 R^2}} \tag{5}$$

Substituting the dependence of R and C on the area A, thickness t, bulk resistivity ρ, and the dielectric constant of the material κ defined by $$R = \frac{\rho t}{A} \tag{6}$$

and $$C = \frac{\kappa \varepsilon_0 A}{t} \tag{7}$$

where electric permittivity constant $\varepsilon_0 = 8.85 \times 10^{-12}$ F/m, the magnitude of the total impedance is given by $$|Z_{tot}| = \frac{\rho t}{A}\sqrt{\frac{1}{1 + \omega^2\left(\frac{\kappa \varepsilon_0 A}{t}\right)^2\left(\frac{\rho t}{A}\right)^2}} = \frac{\rho t}{A}\sqrt{\frac{1}{1 + \omega^2 \kappa^2 \varepsilon_0^2 \rho^2}} \tag{8}$$

According to the AAMI standard, the total impedance of the electrosurgical electrode should be less than 75Ω under normal operating conditions. It is preferred, therefore, that $$\frac{\rho t}{A}\sqrt{\frac{1}{1+\omega^2\kappa^2\varepsilon_0^2\rho^2}} \leq 75\ \Omega \quad (9)$$

We define β as $$\beta = \frac{Z_{tot}}{75\ \Omega} \quad (10)$$

If β<<1, the electrode will have very low impedance compared to the AAMI standard, and the surgeon will not notice any degradation in the electrosurgical cutting power due to the electrode. If β>>1, the electrosurgical electrode will have such a large impedance that the surgeon will no longer be able to perform electrosurgery. Using β in the above inequality, the expression becomes an equality:

$$\frac{\rho t}{A}\sqrt{\frac{1}{1+\omega^2\kappa^2\varepsilon_0^2\rho^2}} = 75\beta \quad (11)$$

It is preferred that self-limiting occur when the electrode has a large electrode area in contact with the patient (FIG. 15); however it is also necessary for self-limiting to occur when the patient only makes contact with a small fraction of the total electrode area (FIG. 11). For self-limiting to work properly, it is necessary for the current density (I/A), where I is the total current through the contact area A of the electrosurgical return electrode, to not exceed a critical value $$\left(\frac{I}{A}\right) \leq \left(\frac{I}{A}\right)_{critical} = 100\ \text{mA/cm}^2 \quad (12)$$

AAMI standards indicate that normal electrosurgical currents are on the order of 500–700 mA. If we set 1000 mA=$I_{max}$ as a safe upper limit as to what one might expect for an above average power surgery, then, in order to return the current to the electrode without exceeding $I_{critical}$, the contact area $A_{contact(min)}$ for traditional electrosurgical return electrodes must have a minimum size:

$$A_{contact\ (min)} \geq \frac{I_{max}}{\left(\frac{I}{A}\right)_{critical}} = \frac{1000\ \text{mA}}{100\ \text{mA/cm}^2} = 10\ \text{cm}^2 \quad (13)$$

It can be appreciated that $I_{max}$ may vary from patient to patient due to changes in the amount of time that the electrode is in contact with the patient, the electrical characteristics of the patient's skin (i.e., resistivity, and the like), the amount of heat being conducted by the patient, the patients initial skin temperature, and the like. With an electrosurgical return electrode designed according to the prior art, in the event that the contact area with the patient reduces below the $A_{contact(min)}$, while maintaining the $I_{max}$, a burn may result because $(I/A)_{critical>}100\text{mA/cm}^2$, which is the burn threshold. In contrast, the present invention limits the possibility of a burn caused from a reduction of the contact area below $A_{contact(min)}$, while also preventing electrosurgical procedures when the contact area is significantly reduced. Therefore, by selecting the appropriate impedance of electrode 60, the current I is always reduced below $I_{max}$ when A<$A_{contact(min)}$.

Figure 12:
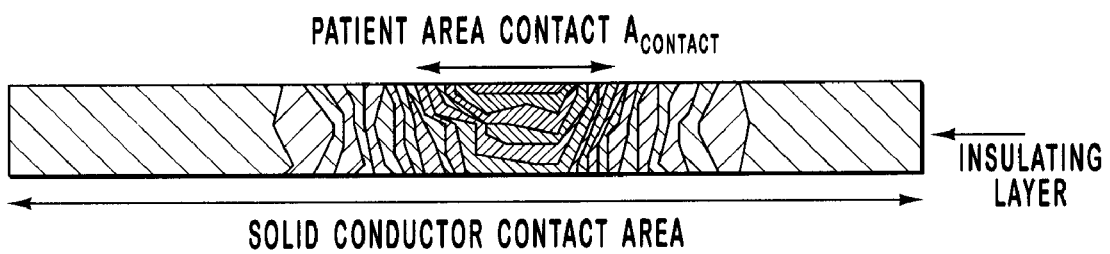
FIG. 12 is a view illustrating current flow density within the electrode when the effective patient contact area is much smaller than the total electrode area.

As such, the impedance between the small electrode with area $A_{contact(min)}$ and the larger metal foil is not simply $$R = \frac{\rho t}{A_{contact\ (min)}} \quad (14)$$

as current can flow through the areas not directly below the patient contact area $A_{contact(min)}$ (FIG. 12). Approximately 10–20% more current flows through the patient contact area $A_{contact}$ than one would expect if the total area of the insulative layer were $A_{contact(min)}$. Equivalently, the effective impedance of the electrode is 10–20% less than what one would normally expect if these edge effects were not present resulting in additional current flow.

As previously mentioned, FIG. 12 reveals current flow distribution through the semi-insulating part of the electrode when the upper contact area with the patient is much smaller than the total electrode surface area. As depicted, current flows through parallel paths around the contact region thus reducing the overall impedance to current flow and thereby increasing the effective area about 10–20 percent. In the Figure, the opaque or heavily hatched region denotes heavier current flow, and the lighter or lightly hatched region denotes lesser current flow.

In order for the electrode to be self limiting, which is efficacious as defined by the AAMI standard, it is preferred that $A_{contact(min)}$ have a value from about 7 cm² to about 22 cm², and more preferably about 10 cm² for electrosurgical currents between 100 mA and about 2,000 mA. Similarly, it is preferred that β range from about 10 to about 50, and more preferably have a value of about 10. Using the various values for $A_{contact(min)}$ and β, it is preferable to solve Equation 11 for the thickness t as a function of the bulk resistivity ρ at different electrosurgical generator frequencies ω, while inserting a factor of 1.2 to account for the edge effects described above. In the particular illustrative embodiment discussed herein, the factor of 1.2 is included within the resistivity and reactance terms of the equation; however, it may be appreciated by one skilled in the art that the factor of 1.2 is geometry dependent for both the resistive and reactance terms and may vary. Additionally, the value of 1.2 is based on the illustrative geometry of the presently described self-limiting electrode and may vary as the geometry of the electrode varies to account for the different edge effects.

The resulting equation (which identifies and defines the interrelationships of parameters affecting self-limitation) is $$t = \frac{1.2A(75\beta)\sqrt{1+\omega^2\rho^2\kappa^2\varepsilon_0^2}}{\rho} \quad (15)$$

Figure 13:
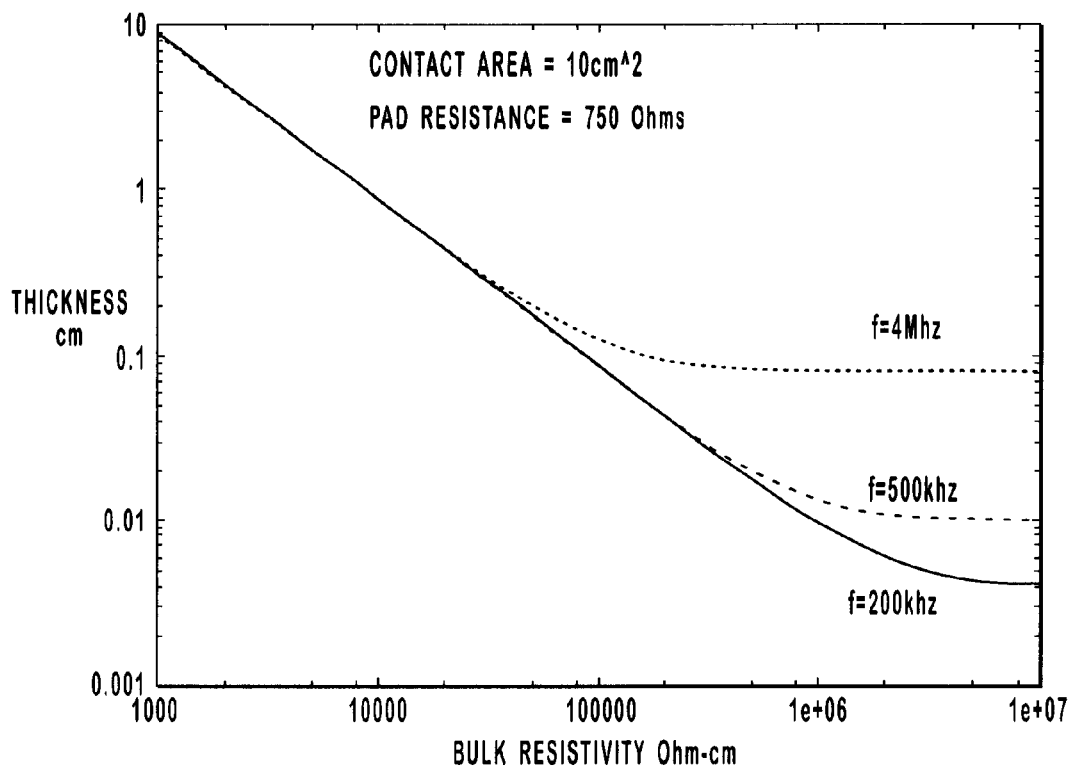
FIG. 13 is a graph depicting variations of bulk resistivity of the resistive layer as a function of electrode thickness for different electrosurgical generator frequencies.

Using Equation 15, FIG. 13 illustrates the variation of minimum bulk resistivity, with electrode thickness, requiring κ=5. The maximum electrode thickness one could imagine using would range from about 0.5 to about 4 inches (about 1.3 cm to about 10.2 cm) and more preferably about 1 inch thick (about 2.5 cm). Above these thicknesses, the electrode may become unwieldy to use and uncomfortable for the patient. Thus, to be self-limiting, the minimum bulk resistivity for an electrode of such thickness is about 4000Ω.cm.

The preceding equations and discussion are representative of the bulk resistivity required for electrode 60 (FIG. 11) to be self-limiting. It may be appreciated, however, that the above analysis may be repeated to obtain the necessary self-limiting impedances for electrodes modeled using primarily capacitive or inductive components, or combinations of resistive, capacitive, and/or inductive components. Therefore, following is a discussion of the self-limiting requirements for the bulk impedance of electrode 60, whether such impedance arises from resistive, capacitive, and/or inductive components of impedance.

OTHER PREFERRED EMBODIMENTS

The self-limiting behavior of the electrosurgical electrode of the present invention results from the existence of sufficient return impedance to make an electrode site burn impossible when the area of contact between the patient and the electrosurgical return electrode is substantially reduced. As shown above, the combination of the maximum electrosurgical currents of 1000 mA coupled with the requirement that the current density be kept below 100 mA/cm² yields a minimum safe contact area of 10 cm².

In general, this requirement can be met with any number of electronic components hooked together in various configurations, including series and parallel combinations of capacitors, resistors, and even inductors, provided that the total impedance presented by the resulting circuit be about 75β or greater when the contact area is reduced to 10 cm².

Define the total impedance of the circuit between the return electrode of the electrosurgical generator and the patient as $Z_{TOT}$. This impedance is generated by the capacitive, resistive, and inductive properties of the materials inserted between the patient and the return electrode. We define the "bulk impedance" of the material η, a volume independent measure of the impedance of the material, that is frequency dependent, as:

$$\eta = \frac{(A)(Z_{TOT})}{t} \tag{16}$$

Where A is the area of the material and t is the thickness. This is analogous to the relationship between the volume dependent ohmic resistance R and the related volume independent characteristic of the resistive material called the "bulk resistivity" ρ described earlier.

One manner to describe the self-limiting requirement is expressed in terms of η:

$$|Z_{TOT}| = \frac{t|\eta|}{A} > 75\beta \tag{17}$$

Or therefore $$|\eta| > \frac{(75\beta)A}{t} \tag{18}$$

For the previous case (minimum bulk resistivity specification) we used $A = A_{contact(min)} = 10$ cm², (about 1.55 inch²), β=10, and $t = t_{max} = 1$ inch (about 2.5 cm), and a factor of 1.2 to account for edge effects to find that for a pure resistive electrosurgical electrode, $$|\eta| > 4000\Omega.cm \tag{19}$$

Therefore, in the purely resistive case, the bulk impedance (η) is identified as the bulk resistivity (ρ) of the conducting material in the electrode. The results in Equation 19, however, generalize to all materials and electrical components, including resistive, capacitive, and inductive components, and any combinations thereof. As long as the bulk impedance of the electrosurgical electrode is greater than 4000Ω.cm, the electrode will be self-limiting, regardless of whether the self-limiting behavior is due to a resistive, capacitive, inductive impedance, or any combination of these impedances.

As alternate illustrative examples, one might construct a self-limiting electrosurgical electrode using a conductive/resistive return plate coated with an insulating (dielectric) material or one might construct a patient gown out of dielectric material and use a metallic or resistive return electrode. The total effect of these devices would be to create a resistive impedance in series with a capacitive impedance.

For the above defined illustrative examples that model the return electrode in terms of resistive and capacitive impedances, the total impedance of the electrosurgical electrode is the sum of the resistive and the capacitive impedances:

$$Z_{TOT} = R + \frac{1}{j\omega C} \tag{20}$$

In terms of the material bulk resistivity, dielectric constant, area, and thickness, the total impedance is:

$$Z_{TOT} = \frac{\rho t}{A} + \frac{t}{j\omega \varepsilon_0 A} \tag{21}$$

By multiplying both sides of the equation by the area A, and dividing by the thickness t, we can derive the bulk impedance η:

$$\eta = \rho + \frac{1}{j\omega\kappa\varepsilon_0} \tag{22}$$

The magnitude of the bulk impedance is:

$$|\eta| = \sqrt{\rho^2 + \frac{1}{(\omega\kappa\varepsilon_0)^2}} \tag{23}$$

If we require $$|\eta| > \frac{(75\beta)(1.2A)}{t} \tag{24}$$

Then $$\frac{A}{t} < \frac{|\eta|}{1.2(75\beta)} = \frac{\sqrt{\rho^2 + \frac{1}{(\omega\kappa\varepsilon_0)^2}}}{1.2(75\beta)} \tag{25}$$

As such, the edge effects reduce the bulk impedance of the electrode by about 10–20 percent, thereby causing a corresponding increase in the effective area of the self-limiting electrode by about 10–20 percent and reduces the possibility of unwanted electrosurgical burns.

Figure 14:
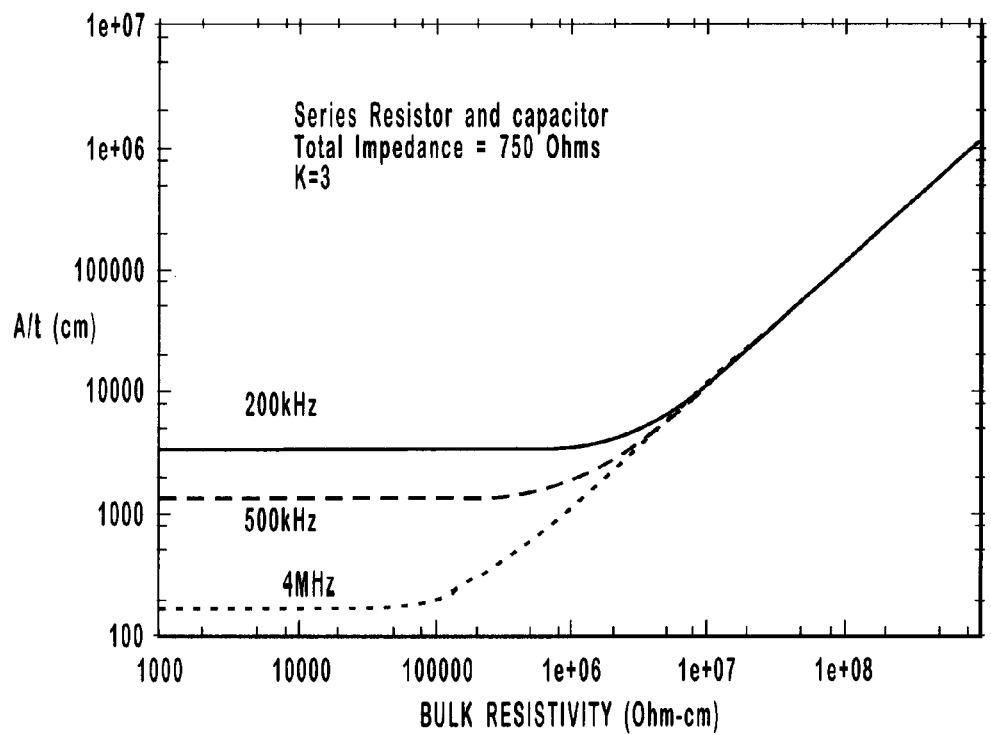
FIG. 14 is a graph showing bulk resistivity as a function of the area divided by the thickness of an electrosurgical return electrode in accordance with the present invention at various electrosurgical frequencies.

FIG. 14 plots A/t vs. bulk impedance η for various electrosurgical frequencies. The y-axis has the minimum ratio of A/t in order to have self-limiting behavior as a function of the bulk impedance. Note that we require bulk impedance always greater than 4000Ω.cm. On the right hand side of the plot, all of the curves merge into one. In this regime, the total impedance of the circuit is dominated by the resistive component and is, hence, independent of frequency. On the left hand side, the circuit impedance is dominated by the capacitive conduction of current. One requires area to thickness ratios of several hundred to about 10,000 in order to provide sufficient total impedance with the low ohmic resistance in this region.

The resulting lowest possible bulk impedance, therefore, is greater than that anticipated by the Twentier U.S. Pat. No. 4,088,133; and, consequently, the self-limiting electrode according to the invention hereof appears to be neither taught nor suggested by known prior art. A product according to the invention hereof can be easily distinguished from previous art through a simple test of the bulk impedance, such as the bulk resistivity of the insulating material, independent of electrode area or electrode thickness.

Interrelationships of Geometries Materials and Power Sources

As mentioned above, FIGS. 11–17 are set forth to define the geometries and characteristics of materials employed to obtain the foregoing self-limiting action. Discussion will be made hereinafter to present illustrative information and an example related to an electrode that may be used for electrosurgical procedures utilizing capacitive conduction while still remaining self-limiting. Although discussion is made herein with respect to an electrosurgical electrode functioning under capacitive conduction, similar illustrative information and examples may be provided for resistive and inductive conduction, as known by one skilled in the art.

Figure 15:
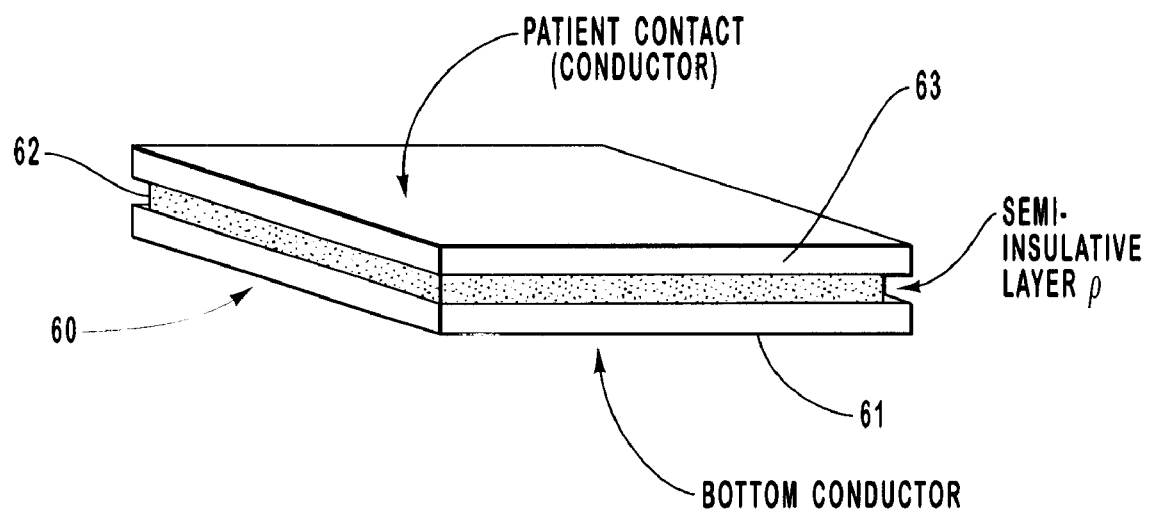
FIG. 15 is a perspective view illustrating, for the purpose of analysis, the circuit equivalent of a patient in operative association with the ohmic and capacitive regions of an electrode according to the invention.
Figure 16:
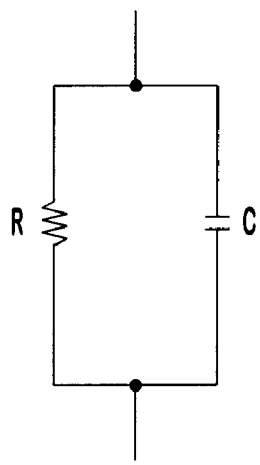
FIG. 16 is a simple electronic schematic circuit equivalent to FIG. 15.

FIG. 15 depicts an electrosurgical electrode 60 consisting of a conductive metal backing 61 and a semi-insulating layer 62 of material with bulk resistivity ρ, thickness t and area A. The electrode is in contact with another conducting layer 63 which represents a patient thereupon. The circuit can be modeled as a resistor R in parallel with a capacitor C (FIG. 16). The resistance R is related to the bulk resistivity ρ, area A, and thickness t by the formula $$R = \frac{\rho t}{A} \tag{26}$$

The capacitance C is approximately related to the area A, thickness t, electric permittivity constant $\epsilon_0 = 8.85 \times 10^{-12}$ F/m and the dielectric constant of the material κ:

$$C = \frac{\kappa \varepsilon_0 A}{t} \tag{27}$$

The magnitude of the capacitor impedance is $$X_C = \frac{1}{\omega C} = \frac{t}{\omega \kappa \varepsilon_0 A} \tag{28}$$

The ratio Y of the current flow due to the capacitive path to the current flow due to the resistive path is $$Y = \frac{\frac{1}{X_c}}{\frac{1}{R}} = \frac{\frac{\omega \kappa \varepsilon_0 A}{t}}{\frac{A}{\rho t}} = \omega \kappa \varepsilon_0 \rho \tag{29}$$

The ratio Y is independent of the electrode area and thickness, depending only upon κ and ρ. For principally capacitive coupling, Y>>1, whereas for principally resistive current, Y<<1. The boundary between the capacitive current and the resistive current is Y=1.

$$1 = 2\pi f \kappa \varepsilon_0 \rho \tag{30}$$

We can use this, along with the value of $\epsilon_D$, to find the necessary values of ρ for capacitive conduction, given nominal values of κ and ω=2πf where f is the electrosurgical generator frequency.

$$\rho = \frac{1}{2\pi f \kappa \varepsilon_0} \tag{31}$$

For most insulating materials, κ ranges from 3 to 5. Commercially available electrosurgical generators presently have operating frequencies ranging from 200 kHz to 4 MHz. For κ=5 and f=4 MHz, it is preferred that $\rho \geq 1 \times 10^5 \Omega$.cm for the electrosurgical electrode to return the majority of its current through capacitive coupling. For κ=3 and f=200 kHz, we require $\rho \geq 3 \times 10^6 \Omega$.cm.

The percentage of total current derived through capacitive coupling is given by $$pct = \frac{\frac{1}{|X_c|^2}}{\frac{1}{|R|^2} + \frac{1}{|X_c|^2}} \tag{32}$$

$$= \frac{|R|^2}{|R|^2 + |X_c|^2}$$

$$= \frac{\left(\frac{\rho t}{A}\right)^2}{\left(\frac{\rho t}{A}\right)^2 + \left(\frac{t}{A\varepsilon_0 \kappa \omega}\right)^2}$$

$$= \frac{\rho^2}{\rho^2 + \left(\frac{1}{\varepsilon_0 \kappa \omega}\right)^2}$$

$$= \frac{(\varepsilon_0 \kappa \omega \rho)^2}{(\varepsilon_0 \kappa \omega \rho)^2 + 1}$$

Figure 17:
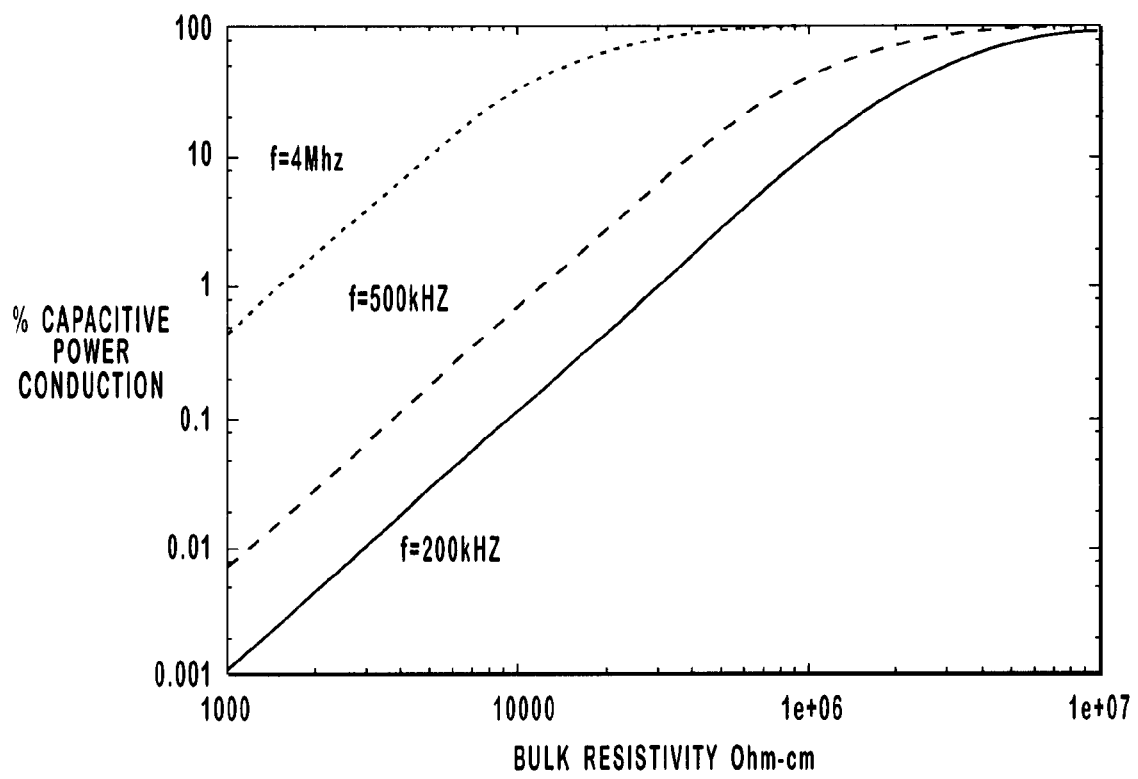
FIG. 17 is a graph depicting percent capacitive power conduction as a function of bulk resistivity of the resistive layer for different electrosurgical operating frequencies.

FIG. 17 illustrates the percentage (%) of capacitive coupling for various frequency electrosurgical generators. At the extreme (4 MHz), a minimum bulk impedance of $10^5 \Omega$.cm is required for the majority of the current to be passed through capacitive coupling.

It will now be evident that there has been described herein an improved electrosurgical return electrode characterized by being generally electrode-shaped and evidencing the features of being self-limiting while being reusable, readily cleanable and obviating the necessity for use of conducting gels or supplementary circuit monitoring equipment.

Although the invention hereof has been described by way of preferred embodiments, it will be evident that adaptations and modifications may be employed without departing from the spirit and scope thereof.

The terms and expressions employed herein have been used as terms of description and not of limitation; and, thus, there is no intent of excluding equivalents, but, on the contrary, it is intended to cover any and all equivalents that may be employed without departing from the spirit and scope of the invention.

What is claimed is:

1. An electrosurgical electrode configured to be disposed beneath a patient during electrosurgery to provide a return path for an electrosurgical current used in electrosurgery, the electrosurgical electrode comprising:
   a sheet of material having an effective bulk resistivity equal to or greater than about 8,000Ω.cm;

an upper surface having sufficient area to limit a current density to safe thresholds while obviating the need for direct contact between the patient and the electrode, wherein the effective impedance of the electrode is inversely proportional to the effective contact area between the patient and the electrode and the electrosurgical electrode being self-limiting so that the electrosurgical current is limited to safe thresholds so as to prevent an undesirable patient burn at a contact area between the patient and the electrode in the event of an accidental reduction in the contact area below a threshold level.

2. The electrosurgical electrode of claim 1, wherein the sheet of material comprises electrically conducting material having an effective bulk resistivity equal to or greater than about 8,000Ω.cm.

3. The electrosurgical electrode of claim 1, wherein the sheet comprises normally insulating material impregnated with electrically conducting fibers to render the sheet to have an effective bulk resistivity equal to or greater than about 8,000Ω.cm.

4. The electrosurgical electrode of claim 1, wherein the sheet comprises a normally insulating material impregnated with electrically conducting carbon black to render the sheet to have an effective bulk resistivity equal to or greater than about 8,000Ω.cm.

5. The electrosurgical electrode of claim 1, wherein the sheet of material has a predetermined thickness and includes a resistive material having a predetermined bulk resistivity, and wherein a relationship of the bulk resistivity, the contact area and the predetermined thickness is defined by the equation $$t = \frac{A(75)\beta\sqrt{1+\omega^2\left(\frac{\rho}{1.2}\right)^2\kappa^2\varepsilon_0^2}}{\rho/1.2}$$

where
t=thickness (cm)
κ=dielectric constant of insulating material
β=total impedance divided by the AAMI standard (75 ohms)
ω=angular frequency of electrosurgical generator (radians/sec)
ρ=bulk resistivity (Ω.cm)
A=electrode area (cm$^2$)
$\varepsilon_o$=electrical permittivity constant (F/cm).

6. An electrosurgical electrode configured to be disposed beneath a patient during electrosurgery to provide a return path for an electrosurgical current used in electrosurgery, the electrosurgical electrode comprising:

a sheet of material having an effective bulk resistivity equal to or greater than about 8,000Ω.cm;

an upper surface having a greater surface area than that of the projected area of the buttocks or torso of a patient allowing the patient to move during the course of a procedure while a sufficient portion of the patient will remain in contact with the electrode such that the effective impedance of the electrode allows sufficient current to permit electrosurgery while self-limiting a current density to safe thresholds so as to prevent an undesirable patient burn at a contact area between the patient and the electrode in the event of an accidental reduction in the contact area below a threshold level, the surface area obviating the need for direct contact between the patient and the electrode, wherein the effective impedance of the electrode is inversely proportional to the effective contact area between the patient and the electrode.

7. The electrosurgical electrode of claim 6, wherein the electrode is sterilizable.

8. The electrosurgical electrode of claim 7, wherein the electrode is washable.

9. The electrosurgical electrode of claim 8, wherein the electrode is reusable.

10. The electrosurgical electrode of claim 9, further comprising an insulating sleeve substantially enclosing the sheet.

11. An electrosurgical electrode configured to be disposed beneath a patient during electrosurgery to provide a return path for an electrosurgical current used in electrosurgery, the electrosurgical electrode comprising:

a sheet of material having an effective bulk resistivity equal to or greater than about 8,000Ω.cm;

an upper surface having sufficient area to self-limit a current density to no more than 100 mA/cm$^2$ so as to prevent an undesirable patient burn at a contact area between the patient and the electrode in the event of an accidental reduction in the contact area below a threshold level while obviating the need for direct contact between the patient and the electrode, wherein the effective impedance of the electrode is inversely proportional to the effective contact area between the patient and the electrode.

12. The electrosurgical electrode of claim 11, wherein the sheet has a surface area equal to or greater than about 100 square centimeters.

13. The electrosurgical electrode of claim 11, wherein the effective impedance of the sheet is within the range of about one to about 250Ω.cm.

14. The electrosurgical electrode of claim 11, wherein the sheet has a surface area within a range from about 100 to 20,000 square centimeters.

15. The electrosurgical electrode of claim 11, wherein the sheet continuously and automatically regulates the electrosurgical current flowing through the electrode.

16. The electrosurgical electrode of claim 15, wherein the electrosurgical electrode is configured to limit the temperature rise of patient tissue in registration with the electrode to six degrees (6°) Celsius when current is flowing through the electrode during a surgical procedure.

17. The electrosurgical electrode of claim 11, wherein the sheet of material comprises electrically conducting material having an effective bulk resistivity equal to or greater than about 8,000Ω.cm.

18. The electrosurgical electrode of claim 11, wherein the sheet comprises normally insulating material impregnated with electrically conducting fibers to render the sheet to have an effective bulk resistivity equal to or greater than about 8,000Ω.cm.

19. The electrosurgical electrode of claim 11, wherein the sheet comprises a normally insulating material impregnated with electrically conducting carbon black to render the sheet to have an effective bulk resistivity equal to or greater than about 8,000Ω.cm.

20. The electrosurgical electrode of claim 11, wherein the electrode is at least one of sterilizable, washable, and reusable.

* * * * *

UNITED STATES PATENT AND TRADEMARK OFFICE
CERTIFICATE OF CORRECTION

PATENT NO. : 6,666,859 B1
DATED : December 23, 2004
INVENTOR(S) : Fleenor et al.

It is certified that error appears in the above-identified patent and that said Letters Patent is hereby corrected as shown below:

Column 5,
Line 18, please change "and so not" to -- and therefore are not --
Line 50, after Equation (1), please add -- ... --

Column 9,
Line 8, after "electrode" change "hereof" to -- thereof --
Line 9, after "according" insert -- to --

Column 10,
Line 57, after "range" remove "of"

Column 14,
Line 62, change "4000 $\Omega.cm$." to -- 4000 $\Omega \cdot cm$. --

Column 16,
Lines 2 and 64, change "4000 $\Omega.cm$." to -- 4000 $\Omega \cdot cm$. --

Column 18,
Line 4, Equation (30), change "1=$2\pi f\kappa\epsilon_o\rho$" to -- 1=$2\pi f\kappa\varepsilon_o\rho$ --
Line 5, after "value of" change "$\epsilon_D$" to -- $\varepsilon_D$ --
Line 16, change "1x$10^5\Omega.cm$" to -- 1x$10^5\Omega \cdot cm$ --
Line 19, change "3x$10^5\Omega.cm$" to -- 3x$10^5\Omega \cdot cm$ --
Line 43, change "$10^5\Omega.cm$" to -- $10^5\Omega \cdot cm$ --
Line 67, change "8000$\Omega.cm$" to -- 8000$\Omega \cdot cm$ --

Column 19,
Lines 16, 21 and 26, change "8000$\Omega.cm$" to -- 8000$\Omega \cdot cm$ --
Line 46, change "($\Omega.cm$)" to -- ( $\Omega \cdot cm$) --
Line 49, change "$\epsilon_0$" to -- $\varepsilon_0$ --
Line 55, change "8000$\Omega.cm$;" to -- 8000$\Omega \cdot cm$; --

UNITED STATES PATENT AND TRADEMARK OFFICE
CERTIFICATE OF CORRECTION

PATENT NO. : 6,666,859 B1
DATED : December 23, 2004
INVENTOR(S) : Fleenor et al.

It is certified that error appears in the above-identified patent and that said Letters Patent is hereby corrected as shown below:

Column 20,
Line 20, change "8000Ω.cm;" to -- 8000Ω • cm; --
Line 36, change "250Ω.cm." to -- 250Ω • cm. --
Lines 51, 56 and 61 change "8000Ω.cm." to -- 8000Ω • cm. --

Signed and Sealed this

Twenty-seventh Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,666,859 B1
DATED : December 23, 2003
INVENTOR(S) : Fleenor et al.

It is certified that error appears in the above-identified patent and that said Letters Patent is hereby corrected as shown below:

Title page,
Item [57], ABSTRACT,
Line 8, change "4000Ω.cm" to -- 4,000 Ω•cm --

Column 9,
Line 38, change "$\epsilon_o$" to -- $\varepsilon_o$ --

Column 12,
Line 60, change "$\epsilon_o$" to -- $\varepsilon_o$ --

Column 15,
Equation 19, change "4000Ω.cm" to -- 4,000 Ω•cm --

Column 17,
Line 43, change "$\epsilon_o$" to -- $\varepsilon_o$ --

Column 18,
Line 5, change "$\epsilon_D$" to -- $\varepsilon_o$ --

Signed and Sealed this

Fifth Day of October, 2004

JON W. DUDAS
*Director of the United States Patent and Trademark Office*